US005897989A

United States Patent [19]
Beecham

[11] Patent Number: 5,897,989
[45] Date of Patent: Apr. 27, 1999

[54] METHOD, APPARATUS AND SYSTEM FOR VERIFICATION OF INFECTIOUS STATUS OF HUMANS

[76] Inventor: James E. Beecham, 8820 Cortile Dr., Las Vegas, Nev. 89134

[21] Appl. No.: 08/686,211

[22] Filed: Jul. 23, 1996

[51] Int. Cl.$^6$ .................................................. C12Q 1/70
[52] U.S. Cl. ........................... 435/5; 435/4; 364/400; 364/409; 364/413; 364/413.01; 382/2; 382/4; 382/115; 382/124; 382/125; 382/126
[58] Field of Search ..................... 364/413, 400, 364/409, 413.01; 382/2, 4, 115, 124, 125, 126; 435/4, 5

[56] References Cited

U.S. PATENT DOCUMENTS

| | | | |
|---|---|---|---|
| 3,648,240 | 3/1972 | Jacoby et al. | 340/163.3 E |
| 4,737,912 | 4/1988 | Ichikawa | 364/413 |
| 4,819,267 | 4/1989 | Cargile et al. | 380/23 |
| 4,888,750 | 12/1989 | Francoeur | 436/501 |
| 4,961,229 | 10/1990 | Takahashi | 381/42 |
| 4,975,969 | 12/1990 | Tal | 382/2 |
| 4,993,068 | 2/1991 | Piosenka et al. | 380/23 |
| 5,012,522 | 4/1991 | Lambert | 382/2 |
| 5,071,168 | 12/1991 | Shamos | 283/117 |
| 5,073,949 | 12/1991 | Takeda et al. | 382/2 |
| 5,073,950 | 12/1991 | Colbert et al. | 382/2 |
| 5,191,611 | 3/1993 | Lang | 380/25 |
| 5,193,541 | 3/1993 | Hatsuwi | 128/630 |
| 5,222,152 | 6/1993 | Fishbine et al. | 382/2 |
| 5,270,167 | 12/1993 | Francoeur | 435/7.21 |
| 5,325,294 | 6/1994 | Keene | 364/413.01 |
| 5,335,288 | 8/1994 | Faulkner | 382/4 |
| 5,359,669 | 10/1994 | Shanley et al. | 382/6 |
| 5,363,453 | 11/1994 | Gagne et al. | 382/5 |
| 5,369,415 | 11/1994 | Richard et al. | 345/6 |
| 5,381,487 | 1/1995 | Shamos | 382/2 |
| 5,465,303 | 11/1995 | Levison et al. | 382/124 |
| 5,479,523 | 12/1995 | Gaborski et al. | 382/159 |
| 5,483,601 | 1/1996 | Faulkner | 382/115 |
| 5,546,471 | 8/1996 | Merjanian | 382/124 |

OTHER PUBLICATIONS

An Excerpt from CCBC Newsletter, Mar. 17, 1996, pp. 1–2.

*Primary Examiner*—Jeffrey Stucker
*Attorney, Agent, or Firm*—Seed & Berry LLP

[57] ABSTRACT

A method and apparatus for collecting medical data from a test subject while preserving anonymity for the test subject. The method includes steps of collecting a sample from the test subject and taking biometric data from the test subject. The biometric data permit a high order of probability of correlation of the test subject with the sample and with test results derived from the sample. The method desirably further includes a step of providing the test subject with a unique correlating code also for permitting unique correlation of the test subject with the sample and with test results derived from the sample, and further desirably includes a step of labeling the sample with information including the biometric data.

39 Claims, 3 Drawing Sheets

METHOD, APPARATUS AND SYSTEM FOR VERIFICATION OF INFECTIOUS STATUS OF HUMANS

BACKGROUND OF THE INVENTION

1. Field of the Invention

This invention relates to a method, apparatus and system for anonymously providing medical data for humans including infectious status.

More particularly, the present invention relates to anonymously providing infectious status data for humans via unforgeable correlation characteristics.

In a further and more specific aspect, the instant invention concerns a method and apparatus for voluntarily and anonymously providing infectious status data for humans and allowing the subject to share that information with a chosen associate or associates.

2. Prior Art

Medical data collection, storage and display systems of great variety in construction and purpose are often employed for medical and non-medical purposes. Examples include the systems described in U.S. Pat. No. 4,737,912 entitled "Medical Image Filing Apparatus", issued to Ichikawa, hereby incorporated herein by reference, directed to a medical image filing and display system and the like.

Another example is described in U.S. Pat. No. 5,193,541 entitled "Health Examination Method And System Using Plural Self-Test Stations And A Magnetic Card", issued to Hatsuwi, hereby incorporated herein by reference. This patent is directed to a system for storing medical data on magnetic media contained on a card, wherein the patient provides samples and the like to a variety of testing stations that also record the self-test data on the card.

A further example is taught in U.S. Pat. No. 5,325,294 entitled "Medical Privacy System", issued to Keene, hereby incorporated herein by reference. This patent describes a system and method for retrieving medical data from a database and sharing these medical data voluntarily with another party while protecting against unauthorized access by unauthorized parties.

A feature common to such systems is a means for identifying a particular patient or client and the associated, relevant medical records.

Human disease status is highly confidential information subject to misuse by any of a variety of agencies or individuals. For example, many doctors will advise patients not to seek human immunodeficiency virus (HIV) testing via the doctor because the records generated in the process of testing for HIV may be used by insurance companies to deny insurance coverage to the individual requesting the test results.

The reasoning seems to be that if the individual sought to ascertain HIV status information, the individual must have reason to suspect a positive HIV status. The individual therefore is adjudged likely (i) to have engaged in high-risk behavior, (ii) to continue to engage in high-risk behavior and (iii) to have an enhanced probability (compared to other population segments) of developing (a) HIV-positive status and (b) later, acquired immune deficiency syndrome (AIDS), presently an almost invariably fatal condition. People may well be denied employment if it is suspected that they are at risk of developing an HIV-positive status or of contracting AIDS subsequent to infection by HIV.

Accordingly, it is desirable, particularly with respect to HIV testing, to be tested in a way that completely protects the individual identity of the test subject. One such system is provided in some states through Planned Parenthood, which (i) collects a blood sample from the test subject and (ii) collects whatever identifying indicia the test subject cares to provide, such as a pseudonym. The agency typically then (iii) links the identifying indicia, the test sample and a unique identifying code or serial number in a computer database or other log and (iv) informs the test subject that test results are to be expected to be available following a set interval of one to two weeks, which interval is for shipping the test sample to a suitable laboratory or other testing facility and receiving the results of the analysis therefrom.

The test sample and code or serial number are then (v) sent to a remote site for testing and analysis. Results are then (vi) sent back to the test site (or any other designated place). The test subject (vii) returns to the test site or goes to a designated office and (viii) is advised of the test results. If warranted, (ix) appropriate counseling is provided along with follow-up services. Additionally, (x) a paper record is often provided with an indication of the test results.

Unfortunately, because the test subject often provides a pseudonym, a third party has no way of knowing that a particular record is actually the product of a test conducted on samples provided by the individual presenting such a record. Moreover, the paper record is easily forged or mutilated to alter the information contained thereon, in part because there is no standard or unforgeable format for such records. In short, this system affords an individual test subject great confidence in both the anonymity and the trustworthiness of the test result, but this system does not provide the test subject with any verifiable way of providing the test results to a third party. Additionally, recent multiple-drug therapies can reduce presence of HIV and indicia of HIV to immeasurably low levels but these therapies introduce detectable levels of drugs into the bloodstream of the test subject.

Further, the situations in which people might meet and desire to know or communicate to each other the status of one another do not lend themselves to accessing of data during the course of normal business hours. Social settings in which persons might meet and form a mutual desire for sexual activity tend to be focused on hours other than normal business hours, for example, in the evening at a nightclub. If there were a method for reliably and anonymously exchanging information such as indicia of HIV-negative status and the date on which the sample providing this result was collected, it would need to be useful in such settings or in conjunction therewith in order to be effective in controlling the spread of this deadly disease.

Accordingly, it is desirable to provide reliable data on health and/or infectious status in an anonymous fashion whereby the person viewing the data has some assurance that the data correspond to the individual with whom they are considering carrying out such activities. However, this alone is not necessarily sufficient because it is desirable to be able to have access to the data on a twenty-four-hour-a-day basis, and also because identification cards and the like may not correspond to the bearer thereof. Therefore, it is appropriate and useful to base the correlation process on parameters unique to the individual whilst continuing to ensure anonymity of the test subject, the test results and the fact that the test subject had the testing performed.

In order to combat these varied problems, some form of correlation that is unique to the individual, that is not based on a photograph or the like of the individual and that does not employ a transferable or forgeable identity device (such as an identity card) is required. The form of correlation needs to be highly reliable and also must operate rapidly in real time to provide "go-no go" identification in a short period of time (e.g., a minute or less).

While the various mentioned prior art devices function as apparatus for collecting, storing and retrieving human medical data, certain inherent deficiencies preclude adequate, satisfactory performance of the purpose of reducing risk of exposure of the individual identities of persons using the system.

It would be highly advantageous, therefore, to remedy the foregoing and other deficiencies inherent in the prior art.

Accordingly, it is an object of the present invention to provide improvements in anonymous human health data collection and retrieval.

Another object of the present invention is the provision of an improved method and apparatus for anonymously providing human health data in a secure and tamper-free fashion that allows a person to share those data with another party.

An additional object of the instant invention is the provision of an improved method and apparatus for providing human health data in a way that allows another party to have great confidence that the data provided are reliable and that they correspond to the party rendering the data available to them.

Still a further additional object of the present invention is to provide an improved method, apparatus and system for anonymously collecting human health data and allowing retrieval of the data in a secure fashion that permits twenty-four hour access thereto.

And another object of the present invention is to provide an improved method, apparatus and system for collecting, storing and retrieving human health data in an anonymous fashion that does not rely on forgeable identification devices.

Still another object of the present invention is the provision of a method, system and apparatus for displaying and sharing human health data with a chosen person or people.

Yet another object of the instant invention is to provide a method, system and apparatus for retrieving human health data in a secure fashion that also provides a high degree of confidence in the test subject of the anonymity of the test subject.

Yet still another object of the instant invention is the provision of a method, system and apparatus for identifying individuals free of HIV indicia in a reliable and anonymous fashion in order to stem the spread of a presently almost invariably fatal disease.

And a further object of the invention is to provide a method, system and apparatus for identifying individuals who are free of HIV indicia and/or indicia of recreational drug usage without risk of compromising the individual's identity.

Still a further object of the immediate invention is the provision of a method, apparatus and system for collecting, storing and retrieving human health data in a secure and tamper-free fashion that also guarantees that the individual retrieving the data is also the individual to whom the human health data are pertinent.

Yet a further object of the invention is to provide a new system and method for anonymously testing for human HIV status and/or antigens or antibodies for human diseases and/or drug levels of therapeutic drugs known to be used in treatment of infectious diseases and/or drug levels of "recreational" drugs.

And still a further object of the invention is the provision of method and apparatus, according to the foregoing, which is intended to allow rapid, real-time access to human health data while preserving the anonymity of the test subject and also providing any other party with whom the test subject chooses to share the data great confidence that the data apply to the test subject.

SUMMARY OF THE INVENTION

Briefly, to achieve the desired objects of the instant invention in accordance with a first preferred embodiment thereof, provided is a method and an apparatus for collecting medical data from a voluntary test subject while preserving anonymity for the test subject. The method includes steps of collecting a sample from the test subject and taking biometric data from the test subject. The biometric data permits correlation of the test subject with the sample and with test results derived from the sample. The method desirably but not essentially includes a step of providing the test subject with a unique correlating code also for permitting unique correlation of the test subject with the sample and with test results derived from the sample. The method also desirably but not essentially includes a step of labeling the sample with information including the biometric data.

The method desirably but not essentially further includes a step of labeling the sample with the unique correlating code, and further desirably but not essentially includes a step of labeling the sample with information including the biometric data.

The method desirably but not essentially further includes steps of analyzing the sample to provide a result, the result for determining infectious status of the test subject and/or presence of antigens or antibodies for human diseases and/or presence of drug levels of therapeutic drugs known to be used in treatment of infectious diseases and/or presence of drug levels of "recreational" drugs, linking the result, the biometric data and the unique correlating code together to form a single record and storing the single record in a database.

In a preferred embodiment, the method includes a step collecting a blood sample from the test subject and the step of taking biometric data from the test subject desirably includes a step of electronically scanning finger print or hand geometry data from the test subject.

Preferably, the steps of collecting a blood sample from the test subject and the step of electronically scanning finger print or hand geometry data from the test subject occur contemporaneously in a single data collection device.

In a second preferred embodiment, the invention contemplates a method for performing medical tests on a voluntary test subject and correlating medical results from the medical tests via correlating indicia while preserving anonymity of the test subject. The method includes steps of receiving a test sample taken from the test subject and reading biometric indicia from a label on the test sample. The biometric indicia permit correlation of the test subject with the sample and with test results derived from the sample. The method also includes steps of analyzing the test sample to derive a result indicative of medical condition of the test subject, linking the biometric indicia and the result to form a single record and recording the single record in a database.

The method desirably but not essentially also includes a step of reading an alphanumeric correlation code from the label. The alphanumeric code provides a unique one-to-one correspondence to the biometric indicia and the test sample. The method optionally includes steps of linking the alphanumeric correlation code, the biometric indicia and the result to form the single record and recording the single record in a database.

The step of analyzing the test sample desirably includes a step of analyzing a blood sample for evidence of presence of human immunodeficiency virus and/or presence of antigens or antibodies for human diseases and/or presence of drug levels of therapeutic drugs known to be used in treatment of infectious diseases and/or presence of drug levels of "recreational" drugs and the step of reading biometric indicia from a label on the test sample desirably includes a step of reading biometric indicia including electronically scanned fingerprint or hand geometry information corresponding to the test subject.

In a further preferred embodiment, the invention includes an apparatus for collecting medical data from a voluntary test subject while preserving anonymity of the test subject. The apparatus includes a sample collection apparatus for collecting a biological sample from the test subject and a biometric data collection device. The biometric data collection device collects biometric data permitting positive correlation of the biological sample with the test subject. The apparatus desirably includes an apparatus for labeling the biological sample with the biometric data and optionally includes an apparatus for providing a unique alphanumeric code to the test subject, the unique alphanumeric code for permitting positive correlation of the biological sample with the unique alphanumeric code. The apparatus for labeling labels the biological sample with the unique alphanumeric code.

In a third preferred embodiment, the sample collection apparatus includes a blood sample collection device and the biometric data collection device includes a fingerprint or hand geometry scanning device. The sample collection apparatus and the fingerprint or hand geometry scanning device comprise a single unit adapted to collect the biometric data and the biological sample contemporaneously.

In a fourth preferred embodiment, the invention includes an apparatus for performing medical testing on a voluntary test subject and correlating medical results from the medical testing with correlation indicia whilst preserving anonymity of the voluntary test subject. The apparatus includes a label reader for reading biometric indicia and a date of sample collection from a label on a biological test sample from the voluntary test subject, an analyzer for analyzing the biological test sample to provide a test result including evidence of infectious status of the voluntary test subject and/or presence of antigens or antibodies for human diseases and/or presence of drug levels of therapeutic drugs known to be used in treatment of infectious diseases and/or presence of drug levels of "recreational" drugs, and a computer coupled to the label reader and to the analyzer. The computer links the biometric indicia from the label reader, the date and the test result to provide a single record and for storing the single record in a database.

In a fifth preferred embodiment, the invention includes method for retrieving medical data from a database. The method includes steps of providing a biometric reading by a user, receiving medical data from a database when the biometric reading positively correlates with a biometric reading associated with the medical data stored in the database and displaying the medical data.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which.

DETAILED DESCRIPTION OF THE PREFERRED EMBODIMENT

Figure 1:
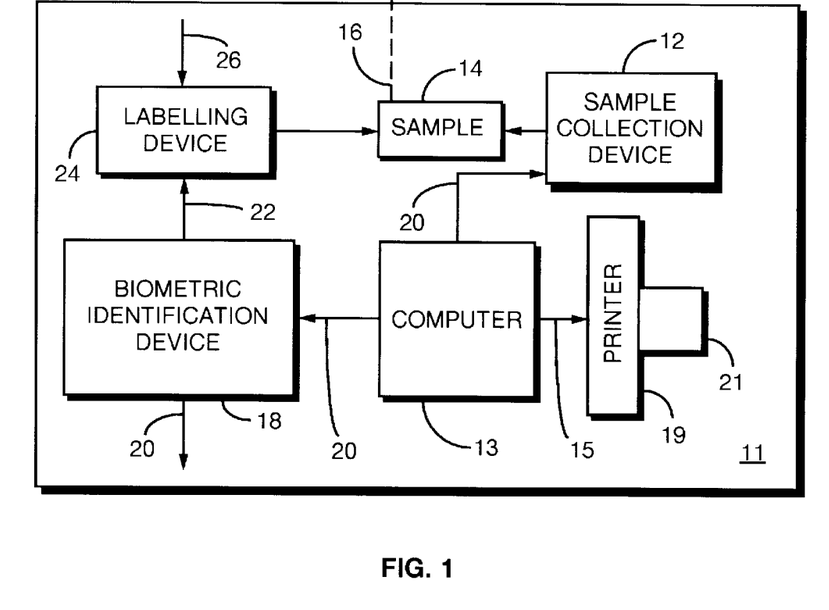
FIG. 1 is a schematic illustration of a collecting station for taking (i) a biological sample from a test subject and (ii) collecting correlating data pertinent to the test subject in accordance with the teachings of the instant invention.
Figure 2:
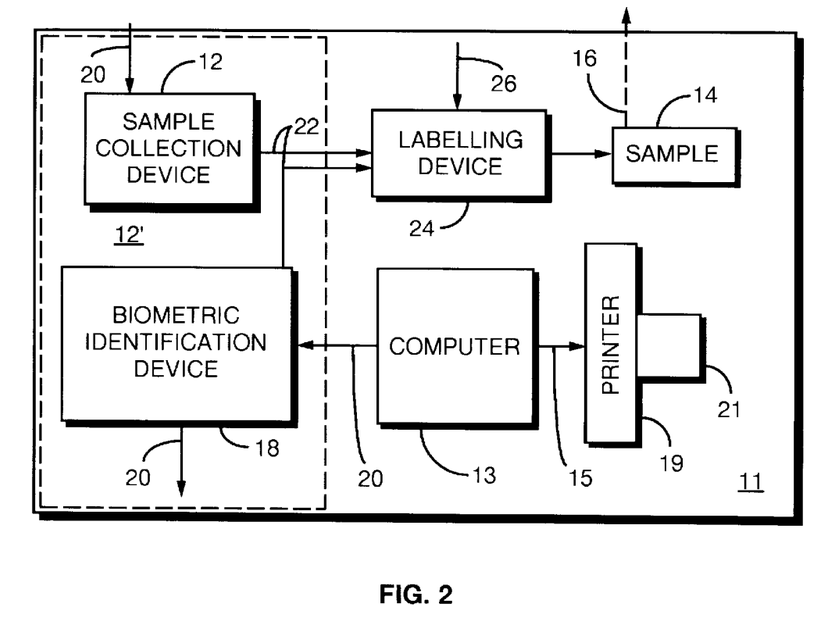
FIG. 2 is a schematic illustration of a collecting station for contemporaneously taking (i) a biological sample from a test subject and (ii) collecting correlating data pertinent to the test subject in accordance with the teachings of the instant invention.

Turning now to the drawings, in which like reference characters indicate corresponding elements throughout the several views, attention is first directed to FIGS. 1 and 2, illustrating a data collection station, generally designated by the reference character 11, for taking (i) a biological sample from a voluntary test subject and (ii) collecting correlating biometric data pertinent to the test subject, and provided with biometric scanner or correlation device 18 in accordance with the teachings of the instant invention. The arrangement of FIG. 2 provides a single apparatus 12' for contemporaneously taking (i) a biological sample from a test subject and (ii) collecting correlating data pertinent to the test subject in accordance with the teachings of the instant invention. This arrangement is preferred for sample collection stations 11 operating without a human caretaker and for maintaining the integrity of the biometric data and sample collection process as is described in more detail below.

It will be appreciated that many different types of biometric scanners 18 could conceivably be employed to realize the desired function for biometric scanner 18. For example, human fingerprints provide unique indicia of identity, while automatic scanning of hand geometry may also be employed for attempting to identify specific individuals.

Techniques for automatically scanning fingerprints are described in U.S. Pat. No. 5,465,303, "Automated Fingerprint Classification/Identification System And Method", Levison et al. and U.S. Pat. No. 5,222,152, entitled "Portable Fingerprint Scanning Apparatus For Identification Verification", issued to Fishbine et al., which patents are hereby incorporated herein by reference.

While such systems are readily used and do not require removal of clothing etc. in most climates, one disadvantage of these types of systems is that certain classes of persons may already have their fingerprints on file. These classes of persons include but are not limited to law enforcement officials, persons holding governmental security clearances, persons holding certain types of permits or personal property for which fingerprints are required and other people. These persons may not feel that a system based on fingerprinting as a means of access provides a degree of anonymity sufficient to promote use of the system. Other possible methods of correlation might include toeprints, which are not usually on file, but this would require a person to remove their footgear in order to use the system and also might lend itself to the spread of annoying conditions such as athlete's foot.

Other types of biometric data successfully used for positive identification or correlation of an individual include dental records, anatomical geometries, retinal patterns, speech recognition or, for that matter, gene sequences or other chemical biodata that uniquely identify a particular individual with a high degree of confidence in the accuracy of the identification.

It will be appreciated that positive correlation of biometric data need not necessarily provide unique identification of a particular individual when a second technique for associating a specific test subject with a specific test result is employed. For example, when a unique serial number known to the test subject is coupled with biometric indicia for providing positive correlation of the test subject and sample, the degree of confidence a third party might have that the test results correspond to the individual could be quite high (even approaching certainty) if the biometric data alone would only provide, for example, a positive correlation carrying at least 95% confidence that the subject was correctly identified (as used herein, the term "positive correlation" means "a high order of probability of identification", i.e., a 95% certainty or better of identification). This means that the biometric data need not be exhaustive and that reduced datasets may be employed for the purpose of reducing the amount of biometric data that must be collected, transmitted and correlated.

Feature recognition based on face geometry is described in U.S. Pat. No. 4,975,969 entitled "Method And Apparatus For Uniquely Identifying Individuals By Particular Physical Characteristics And Security System Utilizing Same", issued to Tal, and in U.S. Pat. No. 5,012,522 entitled "Autonomous Face Recognition Machine", issued to Lambert, which patents are hereby incorporated herein by reference.

Identification techniques based on retinal patterns are described, for example, in U.S. Pat. No. 5,369,415 entitled "Direct Retinal Scan Display With Planar Imager", issued to Richard et al., and in U.S. Pat. No. 5,359,669 entitled "Remote Retinal Scan Identifier", issued to Shanley et al., which patents are hereby incorporated herein by reference. Identification based on speech recognition is described, for example, in U.S. Pat. No. 4,961,229 entitled "Speech Recognition System Utilizing IC Cards For Storing Unique Voice Patterns", issued to Takahashi, which patent is hereby incorporated herein by reference.

Identification based on gene sequences or other chemical biodata that uniquely identify a particular individual with a high degree of confidence in the accuracy of the identification is described in U.S. Pat. No. 5,270,167 entitled "Methods Of Identification Employing Antibody Profiles", and in U.S. Pat. No. 4,880,750 entitled "Individual-Specific Antibody Identification Methods", both issued to Francoeur, which patents are hereby incorporated herein by reference.

An algorithm suitable for searching a database of entries for a match for any of the above-noted biometric classification techniques is described in U.S. Pat. No. 5,479,523, entitled "Constructing Classification Weights Matrices For Pattern Recognition Systems Using Reduced Element Feature Subsets", issued to Gaborski et al.

A preferred form of biometric classification for use with the present invention is automated scanning of hand geometry. Hand geometry scanners are described in, for example, U.S. Pat. No. 5,483,601, entitled "Apparatus And Method For Biometric Identification Using Silhouette And Displacement Images Of A Portion Of A Person's Hand", U.S. Pat. No. 5,335,288, entitled "Apparatus And Method For Biometric Identification", both issued to Faulkner; U.S. Pat. No. 5,073,950, entitled "Finger Profile Identification System", issued to Colbert et al.; U.S. Pat. No. 5,073,949, entitled "Personal Verification Apparatus", issued to Takeda et al.; and U.S. Pat. No. 3,648,240, entitled "Personnel Identification Apparatus", issued to Jacoby et al.

Data collection station 11 also includes sample collection device or station 12 for collecting sample 14. In a preferred embodiment of data collection station 11, collection device 12 is a blood sample collection station. Other types of bodily fluids (semen, saliva etc.) could be employed, however, at the present time, blood samples are preferred for testing uniformity and accuracy.

Additionally, it will be appreciated that sample collection station 12 may be employed, if desired, for conducting additional tests (e.g., for pubic lice, herpes, and/or antigens or antibodies associated with infectious diseases and any other infectious or communicable conditions of the test subject, including those previously successfully treated but identifiable by remaining antibodies or other indicia in samples from the test subject, drugs used to treat sexually transmissible diseases and/or "recreational" drug use, especially that associated with risk of acquiring communicable diseases, for example, via sharing of hypodermic needles) as desired or required. Sample collection station yields sample 14 and sample 14 is then labeled by labeling device 24. Labeling device 24 includes optional input port 26, whereby additional data may be entered (e.g., via a keyboard by medical personnel) for inclusion on the label of sample 14 and/or included with biometric correlation data and test date from biometric correlation device 18. Labeling device 24 may be a laser printer, bar code printer or other printing or labeling device as is well known in the art. Biometric correlation data from biometric correlation device 18, a serial number or other correlating indicia, the date of the test and any other desired data are then linked together and supplied via external link 20 for shipment to database 39 (FIG. 3) via electronic link 20.

In a preferred embodiment of the instant invention, electronic link 20 is an encrypted digital link and may be effected via telephone line, for example. In a preferred embodiment of the instant invention, computer 13 supplies the serial number via link 15 to printer 19, which prints out slip 21 bearing the serial number for later use by the test subject.

The system of FIG. 2, wherein biometric scanner 18 is integrally combined with sample collection device 12 to provide combined scanner/sample collection device 12', is a preferred arrangement for the practice of the instant invention. By collecting sample 14 contemporaneously with biometric indicia, assurance that sample 14 and the labeling biometric indicia correspond to one and the same person is provided without requiring the presence of a human monitor in order to ensure compliance. For example, a small blood sample is taken from the tip of one finger (e.g., the middle finger) during the scanning of biometric data from the test subject's hand or at least during a single insertion of the test subject's hand into combined scanner/sample collection device 12'.

This arrangement avoids a situation that could occur if the test subject were allowed to simply volunteer a previously-collected sample when having biometric data collected. In the latter scenario, there is no assurance that the sample actually came from the test subject, rather than the test subject's friend, child or pet. Apparatus for collection of small blood samples are well known in the medical industry where such procedures have been employed for decades for testing for, for example, phenylketonuria in newborns. Automatic blood sample collection apparatus are well known in the industry.

Figure 3:
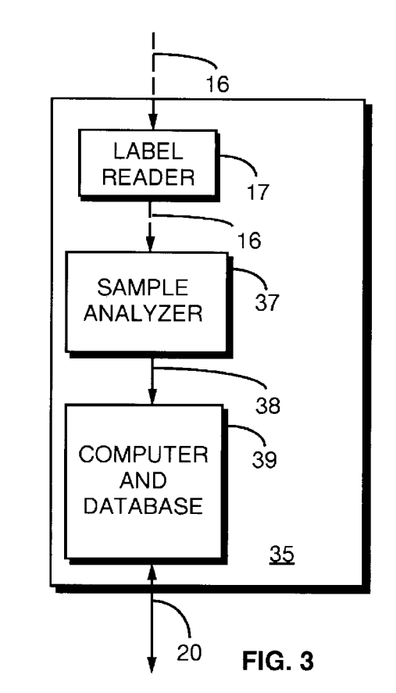
FIG. 3 is a schematic illustration of a biological sample analysis laboratory and computer data entry station of the instant invention.

Labeled sample 14 is transferred via link 16 to sample analysis station 35 of FIG. 3. Transfer via link 16 may be by common carrier to a remote site (e.g., a central testing facility) or to another room in the same facility. This could be effected via the Confide HIV Testing Service™ provided via Direct Access Diagnostics, a subsidiary of Johnson and Johnson, Inc. Direct Access Diagnostics has obtained FDA approval for an over-the-counter blood sample collection kit and testing procedure similar to the testing approach used by Planned Parenthood, i.e., providing the tested individual with great confidence in the accuracy of the test results but not providing a third party with any assurance that the test result corresponds to the presenting individual.

By taking the test sample either under supervision of a neutral medical person or in conjunction with the collection of correlating biometric data, this assurance can be provided to third parties. An additional advantage is realized in that the test subject needn't reveal a personal address or telephone number to an agency such as Direct Access Diagnostics, where this information might be discoverable by others. A further advantage accrues if the test subject can only activate access to the test results by first reviewing the test result with a trained counselor; in-person, face-to-face counseling with appropriate compassion and concern is then available to the test subject in the unfortunate event of a positive test result for HIV or other curable or incurable conditions. Other methods for providing link 16 and suitable testing facilities are available as well.

FIG. 3 is a schematic illustration of biological sample analysis laboratory and computer data entry/storage station 35 of the instant invention. Incoming samples 14 arrive via link 16 and are identified by label reader 17 to determine the serial number or other correlating indicia associated with the biometric data and to be associated with the results of analysis of sample 14. Sample 14 is supplied to sample analyzer 37 via link 16 and an analysis of the contents of sample 14 is performed and communicated to computer/database 39 via link 38. The results of the analysis of sample 14 are coupled to the biometric correlation data and to the serial number by computer and database 39.

Figure 4:
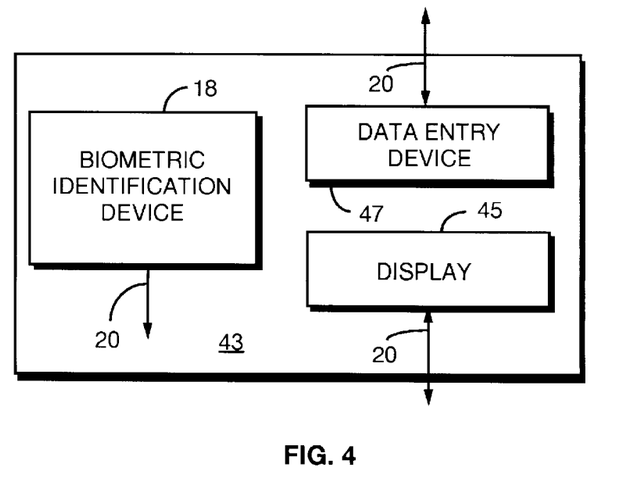
FIG. 4 is a schematic illustration of an embodiment of the data retrieval station of the instant invention.

FIG. 4 is a schematic illustration of an embodiment of data retrieval station 43 of the instant invention. Data retrieval station 43 includes biometric correlation device 18 coupled to database 39 of computer data entry station 35 (FIG. 3) via link 20. Data retrieval station 43 also includes display 45 and desirably includes data entry device 47. Data entry device 47 comprises a keyboard in a preferred embodiment of the instant invention. Data entry device 47 and display 45 are coupled to computer data entry station 35 (FIG. 3) and database 39 via link 20.

Figure 5:
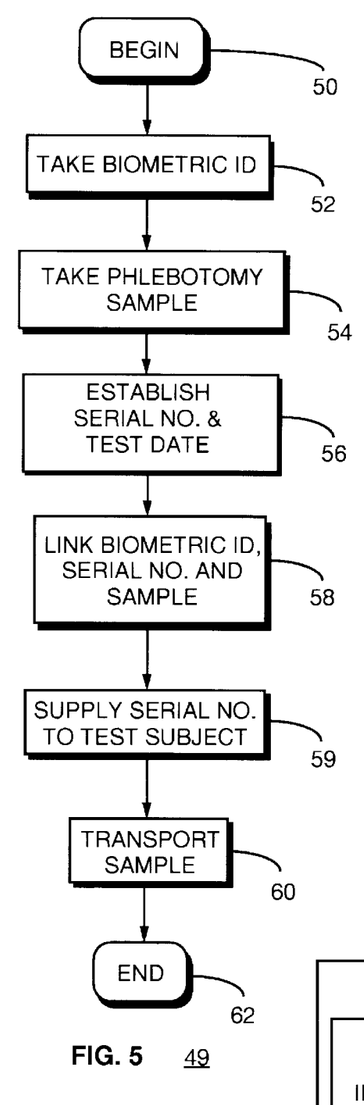
FIG. 5 is a flowchart describing steps involved in collecting (i) a biological sample from a test subject and (ii) collecting correlating data pertinent to the test subject in accordance with the teachings of the instant invention.

FIG. 5 is a flowchart describing steps involved in process 49 for collecting (i) biological sample 14 from a test subject and (ii) collecting correlating data pertinent to the test subject in accordance with the teachings of the instant invention. Process 49 begins (block 50) by taking a biometric correlation reading (block 52) which is digitized for further processing by computer/database 39 (FIG. 3). Phlebotomy sample 14 is collected (block 54), preferably under the supervision of one or more witnesses to both sample collection and the taking of the biometric correlation reading (block 52) in order to ensure the integrity of the data collection and collation process.

Alternatively, sample collection (block 54) may be automated by, for example, combining a retinal scan with an expectorate collection device or blood sample collection device such that sample 14 could only have come from the individual test subject from whom biometric correlation data were collected. Similarly, a fingerstick blood sample collected simultaneously with a finger print by drawing sample 14 from the finger from which the fingerprint is being taken and at the same time as the fingerprint is taken provides similar assurances. These methods have the advantage of allowing the sample collection station to operate without requiring human operators while still protecting the integrity of the system, i.e., a third party could still reasonably have great confidence that the medical information derived from sample 14 corresponds to the individual providing matching biometric data.

A numeric correlation number or serial number is assigned (block 56) and this may be effected via either computer 13 within station 11 (FIGS. 1, 2) or by computer/database 39 of computer data entry station 35 (FIG. 3), with the latter being a preferred arrangement. The serial number, biometric data, test date and sample are linked (block 58) by (i) printing an correlating label on sample 14 via labeling device 24 (FIGS. 1, 2) and (ii) transmission of the serial number, test date and biometric data via link 20 to computer/database 39 (FIG. 3). The serial number is desirably but optionally made available to the test subject (block 59) via slip 21 from printer 19 (FIGS. 1, 2). Labeled sample 14 is then transported (block 60) via link 16 (FIGS. 1, 2) to biological sample analysis laboratory and computer data entry station 35 (FIG. 3). The data collection process then ends (block 62).

Figure 6:
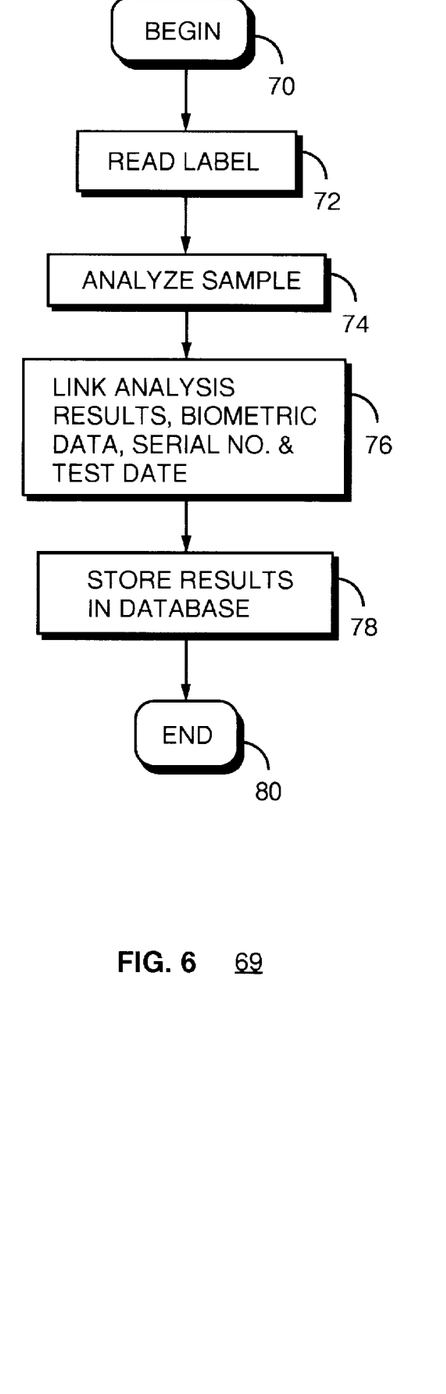
FIG. 6 is a flowchart describing steps involved in biological sample analysis laboratory and computer data entry in accordance with the teachings of the instant invention.

FIG. 6 is a flowchart describing steps involved in biological sample analysis and computer data entry in biological sample analysis laboratory and computer data entry station 35 (FIG. 3) in accordance with the teachings of the instant invention. Process 69 begins (block 70) when incoming samples 14 are transported via link 16 to label reader 17 (FIG. 3) and the serial number and/or biodata and test date on the label of sample 14 are read (block 72) by label reader 17 (FIG. 3). Sample 14 is analyzed (block 74) to determine infectious status, presence of antigens or antibodies associated with past or present infectious disease of the test subject and/or presence of therapeutic or "recreational" drugs. The results of the analysis are linked to the serial number, sample collection date and biometric correlation data (block 76) and are stored (block 78) in database 39 (FIG. 3). Analysis process 69 then ends (block 80).

Figure 7:
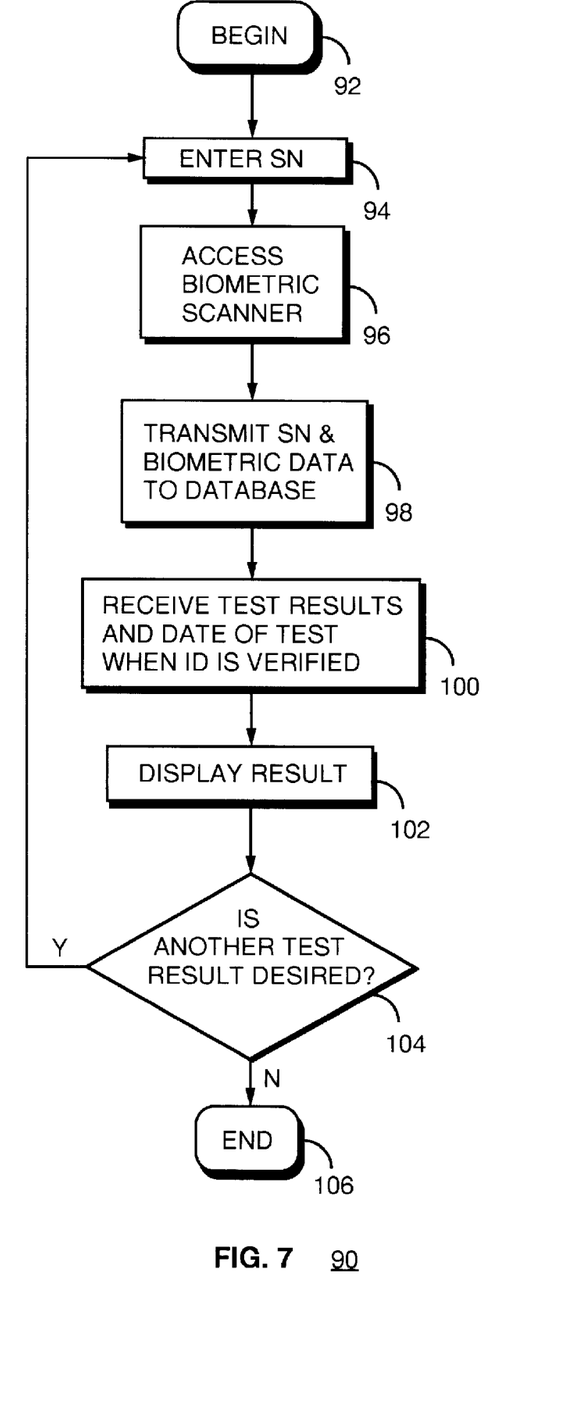
FIG. 7 is a flowchart describing steps involved in secure data retrieval in accordance with the teachings of the instant invention.

FIG. 7 is a flowchart describing steps involved in secure data retrieval process 90 in accordance with the teachings of the instant invention. Data retrieval process 90 begins (block 92) with at least two parties (herein designated "A" and "B") who approach data retrieval station 43 (FIG. 4). "A" and "B" could, for example, be a couple who have recently met at a nightclub and who may have expressed mutual interest in sexual activity but who may also have concerns about the infectious status and/or drug treatment status of each other. "A" enters a serial number SN (block 94) via data entry device 47 (FIG. 4) and also accesses (block 96) biometric correlation device 18 (FIG. 4). Results are transmitted (block 98) to computer/database 39 (FIG. 3) via link 20. When a match is achieved between the serial number and biometric correlation (collectively referred to as "ID") sent from data retrieval station 43 (FIG. 4) with those data stored in biological sample analysis laboratory and computer data entry station 35 (FIG. 3), the test results and date of the test are transmitted back via link 20 and are received (block 100) by data retrieval station 43 (FIG. 4). These results and the date of sample collection are then displayed (block 102) on display 45 (FIG. 4), where "A" and/or "B" may view them.

Data retrieval station 43, after a suitable interval or in response to signals from data entry device 47 (FIG. 4), then determines if a second set of data (corresponding to "B" in this example) are desired. When a second set of data are desired, process 90 loops back to entry of a second serial number (block 94) via data entry device 47 (FIG. 4) followed by "B's" accessing (block 96) biometric correlation device 18 (FIG. 4). Results corresponding to "B" are transmitted (block 98) to computer/database 39 (FIG. 3) via link 20. When a match is achieved between the serial number and biometric correlation (collectively referred to as "ID") sent from data retrieval station 43 (FIG. 4) with those data stored in biological sample analysis laboratory and computer data entry station 35 (FIG. 3), the test results and date of sample collection are transmitted back via link 20 and are received (block 100) by data retrieval station 43 (FIG. 4). These results and the date of the sample collection are then displayed (block 102) on display 45 (FIG. 4), where "A" and/or "B" may view them. When another set of data are not desired, the display is blanked (erased) and process 90 ends.

It will be appreciated that it is not to A's or B's advantage to present themselves in the above-described setting in order to learn the status of the test results for the first time. Additionally, it is desirable to provide counseling for persons who test positive, particularly for HIV, and for test results where there is a possibility of an indeterminate test result or of a false positive. Suitable compassion and counseling can be guaranteed if access to the system is only activated by mandatorily requiring the individual to present him- or her-self at a data retrieval station 43 where the individual and the counselor play the roles of "A" and "B" and review A's or B's test results together in a private setting.

The foregoing detailed description of the instant invention for the purposes of explanation have been particularly directed toward separate facilities for data storage and data retrieval. It will be appreciated that the invention is equally useful for systems where data storage is also performed at each data retrieval station, for example.

It will be appreciated that a system for anonymously testing for infectious disease and/or associated antigens or antibodies and/or other therapeutic or "recreational" drugs has been described that does not require the test subject to carry any identification card or to provide any photograph or home address to the system has been described. The system permits twenty-four hour access to the data in a fashion that (i) provides high credibility to the user as to the accuracy of the test result and the applicability of the test result to the user and (ii) provides high credibility to another person that the test results and test sample collection date correspond to the observable user and accurately reflect the infectious/communicable status of the test subject and/or presence of associated antigens or antibodies and/or other therapeutic or "recreational" drugs as of the date of sample collection, without compromise of the identity of the user or of the another.

It will be appreciated that need for a serial number or at least need for the test subject to have any knowledge of a serial number could be eliminated by employing the biometric data alone as means for accessing the system. However, use of a serial number does require that the parties employing data retrieval station 43 (FIG. 4) both be conscious and also requires voluntary compliance with the data retrieval process. Use of "stress codes" (i.e., codes which inactivate the opening of a closed area and also silently notify authorities) in security systems is widespread and similar procedures may be incorporated into the system of the instant invention in order to obviate abuse of the system or of users of the system. Accordingly, use of a serial number in data retrieval is desirable.

Various changes and modifications to the embodiment herein chosen for purposes of illustration will readily occur to those skilled in the art. For example, other types of diseases may be tested for, to effectuate a combination of capabilities as may be desired for a specific application. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A method for restricting access to medical data from a test subject, said method comprising steps of:

collecting a sample from said test subject; and taking biometric data from said test subject contemporaneously with said step of collecting a sample, said biometric data for permitting a high order of probability of correlation of said test subject with test results derived from said sample.

2. The method of claim 1, further including a step of providing said test subject with a unique correlation code for permitting unique correlation of said test subject with said test results derived from said sample.

3. The method of claim 1, further including a step of labeling said test results with information including data corresponding to said biometric data.

4. The method of claim 1, further including steps of:

analyzing said sample to provide said test results, said test results for determining infectious status of said test subject and/or presence of antigens or antibodies associated with infectious disease and/or presence of therapeutic or "recreational" drugs;

reviewing said test results by a trained counselor to provide a medical opinion;

linking said test results, said medical opinion and data corresponding to said biometric data together to form a single record; and storing said single record in a database.

5. The method of claim 1, further including a step of labeling said sample with information including said biometric data.

6. The method of claim 1, further including steps of:

analyzing said sample to provide said test results, said test results for determining infectious status of said test subject and/or presence of antigens or antibodies associated with infectious disease and/or presence of therapeutic or "recreational" drugs;

linking said test results and data corresponding to said biometric data together to form a single record; and storing said single record in a database.

7. The method of claim 1, wherein:

said step of collecting a sample from said test subject includes a step of collecting a body fluid sample from said test subject; and said step of taking biometric data from said test subject includes a step of electronically scanning fingerprint data from said test subject.

8. The method of claim 7, wherein said steps of collecting a body fluid sample from said test subject and said step of electronically scanning fingerprint data from said test subject occur contemporaneously.

9. The method of claim 7, wherein said steps of collecting a body fluid sample from said test subject and said step of electronically scanning fingerprint data from said test subject occur simultaneously and are performed by a single collection device.

10. A method for performing medical tests on a voluntary test subject and correlating results from said medical tests via correlating indicia to include biometric indicia from said test subject, said method comprising steps of:

receiving a test sample taken from said test subject;

reading label data corresponding to said biometric indicia from a label on said test sample, wherein collection of said biometric indicia and said test sample were contemporaneous, said label data for permitting a high order of probability of correlation of said test subject with said sample and with test results derived from said sample;

analyzing said test sample to derive said test results indicative of medical condition of said test subject;

linking said label data and said test results to form a single record; and recording said single record in a database.

11. The method of claim 10, wherein said step of analyzing said test sample includes a step of analyzing a body fluid sample for evidence of presence of human immunodeficiency virus and/or presence of antigens or antibodies associated with infectious disease and/or presence of therapeutic or "recreational" drugs.

12. The method of claim 10, wherein said step of reading label data from a label on said test sample includes a step of reading data corresponding to electronically scanned eye data from said test subject.

13. The method of claim 10, further comprising steps of:

reviewing said test results by a trained party to provide a medical opinion regarding said test results;

linking said medical opinion to said test results to form a single record; and recording said single record in a database.

14. The method of claim 13, wherein:

said step of analyzing said test sample includes a step of analyzing a blood sample for evidence of presence of human immunodeficiency virus and/or presence of antigens or antibodies associated with infectious disease and/or presence of therapeutic or "recreational" drugs; and said step of reading label data from a label on said test sample includes a step of reading data corresponding to biometric indicia including electronically scanned fingerprint information corresponding to said test subject.

15. An apparatus for collecting medical data from a voluntary test subject, said apparatus comprising:

a sample collection apparatus for collecting a biological sample from said test subject; and a biometric data collection device, said biometric data collection device for collecting biometric data contemporaneously with collecting said biological sample, said biometric data permitting a high order of probability of positive correlation of said medical data derived from testing said biological sample with said test subject.

16. The apparatus of claim 15, further comprising an apparatus for associating said medical data with data corresponding to said biometric data.

17. The apparatus of claim 16, further comprising an apparatus for providing a unique alphanumeric code for permitting unique correlation of said biological sample with said unique alphanumeric code, wherein said unique alphanumeric code labels said biological sample.

18. The apparatus of claim 15, wherein said sample collection apparatus includes a body fluid sample collection device, said biometric data collection device includes a fingerprint scanning device and said sample collection apparatus and said fingerprint scanning device comprise a single unit.

19. The apparatus of claim 15, wherein said sample collection apparatus includes a blood sample collection device, said biometric data collection device includes a fingerprint scanning device and said sample collection apparatus and said fingerprint scanning device comprise a single unit adapted to collect said biometric data and said biological sample such that collection of said biometric data is temporally coincident with collection of said biological sample.

20. An apparatus for performing medical testing on a voluntary test subject and correlating test results from said medical testing with correlation indicia, said apparatus comprising:

a label reader for reading data corresponding to biometric indicia from a label on a biological test sample from said voluntary test subject, wherein collection of said biometric indicia was contemporaneous with collection of said biological test sample;

an analyzer for analyzing said biological test sample to provide said test results, said analyzer coupled to said label reader; and a computer coupled to said label reader and to said analyzer, said computer for linking said data corresponding to said biometric indicia from said label reader and said test result to provide a single record and for storing said single record in a database.

21. The apparatus of claim 20, wherein said label reader additionally reads an alphanumeric code from said label and said computer links said data corresponding to said biometric indicia, said test result and said alphanumeric code to provide said single record.

22. A method for retrieving a user's medical data from a database, said method comprising steps of:

providing a first biometric reading by a first user;

receiving said first user's medical data from said database when said first biometric reading positively correlates with said first user's medical data stored in said database; and displaying said first user's medical data, wherein said first user's medical data from said step of receiving said first user's medical data from said database when said first biometric reading positively correlates with said first user's medical data stored in said database were provided by a process comprising steps of:

collecting a sample from said first user;

taking first biometric data from said first user contemporaneously with collecting a sample from said first user, said first biometric data for permitting a high order of probability of correlation of said first user with said sample and with test results derived from said sample; and linking said first user's medical data with information corresponding to said first biometric data.

23. The method of claim 22, wherein said step of displaying said medical data includes a step of displaying a date of collection of a sample from which said medical data are derived.

24. The method of claim 22, wherein said step of providing a first biometric reading by a first user comprises a step of providing fingerprint data of said first user.

25. The method of claim 24, wherein said step of displaying said medical data includes steps of:

determining from said first user's medical data if said first user has received counseling to obtain a medical opinion regarding said medical data;

displaying said first user's medical data when said determining step indicates that said first user has received counseling to obtain a medical opinion regarding said medical data; and refraining from displaying said first user's medical data when said determining step indicates that said first user has not received counseling to obtain a medical opinion regarding said medical data.

26. The method of claim 22, wherein said step of collecting a sample from said first user includes a step of collecting a body fluid sample from said first user.

27. The method of claim 22, wherein said first user's medical data from said step of receiving said first user's medical data from said database when said first biometric reading positively correlates with said medical data stored in said database were provided by a process comprising steps of:

analyzing said sample to provide said first user's medical data, said medical data for determining infectious status of said first user and/or presence of antigens or antibodies associated with infectious disease and/or presence of therapeutic or "recreational" drugs;

linking said first user's medical data and said information corresponding to said first biometric data together to form a single record; and storing said single record in a database.

28. The method of claim 22, wherein said step of taking biometric data from said first user includes a step of electronically scanning fingerprint data from said first user.

29. The method of claim 22, wherein said step of receiving said first user's medical data from a database includes a step of receiving medical data describing a condition including one chosen from a group consisting of: HIV status of said first user, infectious status of said first user, presence of antigens or antibodies associated with infectious disease and presence of therapeutic or "recreational" drugs describing medical status of said first user providing said first biometric reading.

30. The method of claim 22, further comprising steps of:
providing a second biometric reading by a second user;
receiving said second user's medical data from said database when said second biometric reading positively correlates with said medical data stored in said database; and
displaying said second user's medical data.

31. The method of claim 30, wherein said step of providing a second biometric reading by a second user comprises a step of providing fingerprint data of said second user.

32. The method of claim 30, wherein said step of receiving said second user's medical data from said database includes a step of receiving said second user's medical data describing a condition including one chosen from a group consisting of: HIV status of said second user, infectious status of said second user, presence of antigens or antibodies associated with infectious disease and presence of therapeutic or "recreational" drugs, describing medical status of said second user providing said second biometric reading.

33. A method for providing medical test results wherein said medical test results are retrieved from a database in correspondence with biometric indicia of a sample donor, wherein said medical test results derive from analysis of a biological sample donated by said sample donor, wherein said biological sample is linked to said sample donor biometric indicia prior to said biological sample analysis.

34. The method of claim 33, wherein said medical test results are retrieved at least partly in response to input of biometric data from said sample donor.

35. A system for storage and retrieval of biological sample test data, wherein:

a first test datum derived from testing of a first biological sample from a first user/donor is stored in a database, wherein collecting said first biological sample from said first user/donor and taking biometric indicia from said sample donor were temporally coincident;

a second test datum derived from testing of a second biological sample from a second user/donor is stored in said database;

said first user/donor is enabled to retrieve and share said first test datum by a retrieval procedure including a step of inputting data corresponding to said biometric indicia of said first user/donor; and said second user/donor is enabled to retrieve and share said second test datum by a retrieval procedure including a step of inputting data corresponding to biometric indicia of said second user/donor.

36. The system of claim 35, wherein:
said first biological sample is a body fluid sample taken from said first user/donor;
said second biological sample is a body fluid sample taken from said second user/donor;
said data corresponding to biometric indicia of said first user/donor includes data corresponding to a fingerprint of said first user/donor; and
said data corresponding to biometric indicia of said second user/donor includes data corresponding to a fingerprint of said second user/donor.

37. The system of claim 35, wherein:
a first list of persons enabled to retrieve said first test datum is limited to said first user/donor; and
a second list of persons enabled to retrieve said second test datum is limited to said second user/donor.

38. The system of claim 35, wherein a means of storage of biological sample test data includes linking said biological sample test data with data corresponding to biometric indicia taken from a user/donor whose medical condition is described at least in part by said biological sample test data.

39. The system of claim 35, wherein:
said first user/donor is only enabled to retrieve and share said first test datum when said first test datum is linked to information indicating that said first user/donor has previously been counseled regarding said first test datum; and
said second user/donor is only enabled to retrieve and share said second test datum when said second test datum is linked to information indicating that said second user/donor has previously been counseled regarding said second test datum.

* * * * *